(12) United States Patent
Mayllott et al.

(10) Patent No.: US 6,576,266 B1
(45) Date of Patent: Jun. 10, 2003

(54) PLANT EXTRACT BASED ON GLYCERIDES, A METHOD FOR THE PREPARATION OF THIS EXTRACT AND A COSMETIC COMPOSITION CONTAINING THE SAME

(75) Inventors: Jean-Mathieu Mayllott, Vaduz (LI); Maksymilian Stephodie, Vaduz (LI)

(73) Assignee: Sodic SA, Crans sur Sierre (CH)

( * ) Notice: Subject to any disclaimer, the term of this patent is extended or adjusted under 35 U.S.C. 154(b) by 0 days.

(21) Appl. No.: 09/536,696

(22) Filed: Mar. 28, 2000

(30) Foreign Application Priority Data

Mar. 30, 1999 (CH) .................................. 598/99

(51) Int. Cl.$^7$ .................. A61K 35/78; A01N 43/04; A01N 57/26; A01N 25/00
(52) U.S. Cl. .................. 424/725; 424/750; 514/25; 514/78; 514/783; 514/786; 514/937
(58) Field of Search .................. 424/195.1, 35, 424/85, 401, 439, 455, 420, 70.1, 9.321, 283.1, 78.02, 725, 750, 757, 777, 774, 755, 450; 514/78, 25, 783, 786, 937

(56) References Cited

U.S. PATENT DOCUMENTS

| 4,377,567 A | | 3/1983 | Geho |
|---|---|---|---|
| 4,702,915 A | * | 10/1987 | Keri et al. |
| 5,466,782 A | * | 11/1995 | Rousset |
| 5,688,528 A | * | 11/1997 | Carlsson et al. |
| 5,885,582 A | * | 3/1999 | O'Reilly |
| 6,022,561 A | * | 2/2000 | Carlsson et al. |
| 6,045,828 A | * | 4/2000 | Bystrom et al. |

FOREIGN PATENT DOCUMENTS

| FR | 2 730 409 | | 8/1996 |
|---|---|---|---|
| JP | 63-126820 | | 5/1988 |
| JP | 5-003750 | | 1/1993 |
| JP | 7-155151 | | 6/1995 |
| JP | 078188044 A | * | 7/1995 |
| JP | 9-234357 | | 9/1997 |
| WO | WO 88/08253 | | 11/1988 |
| WO | WO 90/11069 | | 10/1990 |
| WO | WO 95/20944 | | 8/1995 |
| WO | WO 95/20945 | | 8/1995 |
| WO | WO 96/01637 | | 1/1996 |
| WO | WO 96/19199 | * | 6/1996 |
| WO | WO 96/38160 | * | 12/1996 |
| WO | WO 97/10050 | | 3/1997 |
| WO | WO 99/65459 | * | 12/1999 |

OTHER PUBLICATIONS

M.H. Jee, "A new emulsifier from oats", XP–002127532, Abstract No. 166556, vol. 128, No. 14, Apr., 1998.
Tomita et al., "Physiological characteristics of a halo–tolerant yeast Zygosaccharomyces rouxii. 2. Film–forming strains grown on salty foods", XP–002127533, Abstract No. 74426, vol. 128, No. 7, Feb., 1998.
Tokuda et al., "Inhibition of 12–O–tetradencanoylphorbol–13–acetate promoted mouse skin papilloma by digalactosyl diacylglycerols from the fresh water cyanobacterium Phormidium tenue", XP–002127534, Abstract No. 48539, vol. 125, No. 5, Jul., 1996.
Database WPI, XP–002127535, Derwit Publications Ltd., Feb., 1993.
Takashi et al., "Foaming power and emulsifying properties of the hydrolyzates by lipase from Rhizopus arrhizus on digalactosyldiacylglycerol and trigalactosyldiacylglycerol extracted for pumpkin", XP–00127531, Abstract No. 138546, vol. 130, No. 11, Mar., 1999.

* cited by examiner

Primary Examiner—Christopher R. Tate
Assistant Examiner—Michele C. Flood
(74) Attorney, Agent, or Firm—Young & Thompson

(57) ABSTRACT

The present invention is concerned with a plant extract comprising a mixture of di-O-D-galactosyl-di-O-acylglyceride with phytosphingolipids and phospholipids, as well as with a method for the preparation thereof through a physical extraction in the presence of water and ethanol. Such an extract can be used, in particular, in pharmaceutical, cosmetic and food compositions.

10 Claims, No Drawings

PLANT EXTRACT BASED ON GLYCERIDES, A METHOD FOR THE PREPARATION OF THIS EXTRACT AND A COSMETIC COMPOSITION CONTAINING THE SAME

The present invention is concerned with a plant extract based on glycerides, a method for the preparation of this extract, as well as a cosmetic composition and a food composition containing said extract.

The most common of glycolipids is the di-O-D-galactosyl-di-O-acylglyceride, also called GalDAG or, more often, Dgdg, which constitutes from 30 to 40% in weight of lipid, membranes. This glyceride was isolated in 1967 by chromatography from human brain and from spinach leaves.

Specifically, the 2,3-di-O-(fatty acid acyl)-1-O-[6'-O-α-D-galactopyranosyl-β-galactopyranosyl]-D-glycerine is described by the following formula:

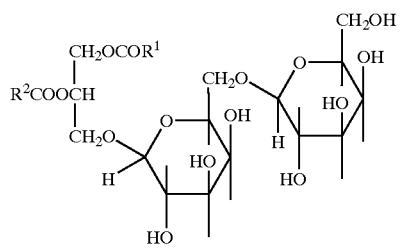

wherein $R^1$ and $R^2$ are acyl groups derived from fatty acids and are selected from linoleyl, palmityl, oleyl and stearyl.

Now, the present inventor has shown that these glycolipids and, more particularly, plant extracts containing Dgdg bound to phytosphingolipids and to phospholipids exhibit moisturising properties, elastase inhibiting properties and collagenase inhibiting properties, wound-healing properties, free radical scavenging properties and they can be used as a vector for introducing bound active ingredients into the intercellular space of skin conjunctive tissue. These properties are particularly useful in cosmetics compositions used for skin, mucosa and hair care, as well as in food compositions and/or dietetic compositions.

Further, the di-O-D-galactosyl-di-O-acylglyceride offers the advantage that it originates from the vegetal kingdom, which eliminates the drawbacks associated with the use of products originating from the animal kingdom, in particular the risks arising from bovine diseases (mad cow disease) caused by certain types of prions which, under specific conditions not yet fully elucidated can cause in humans the Creutzfeld-Jakob disease.

Accordingly, a first object of the present invention is a plant extract which contains a mixture of di-O-D-galactosyl-di-O-acylglyceride with phytosphingolipids and phospholipids.

The second object of this invention is a method for obtaining said vegetal extracts, which is characterised in that it comprises a physical extraction operation in which water and ethanol are the solvent which is used.

Finally a further object of the present invention is to provide a cosmetic composition and a food composition containing said plant extract.

The plants which can be used to obtain the extract according to the invention include generally all the cereals (wheat, barley, rye, oats, corn, sorghum), with wheat being preferably used. Certain beans of dicotyledone plants (soy beans, peanuts), the mesocarp of the fruits of the oil-palm fruits and of the fruits of the avocado tree, as well as leaves rich in chromoplasts of spinach, cabbage and peas can also be used.

The protein portion of wheat grains contains from 5 to 10% lipids in the form of vesicles embedded in a protein network. These lipids include 70% of polar lipids. It is preferable to carry out the extraction on wheat grains, because an extract rich in di-O-D-galactosyl-di-O-acylglyceride can then be obtained.

The exact composition of the extract according to the invention depends of course on the nature and on the origin of the plant material: for example, it is well known that soy beans have a content of di-O-D-galactosyl-di-O-acylglyceride which is substantially lower than wheat, but the extract can generally contain between 10 and 50% Dgdg.

Concerning the preparation method, owing to the use of cold ethanol, it enables the extraction of the surface lipid fraction, as well as that of the lipids bound to the protein network. The choice of the ratio of the weight of the plant material to the weight of the solvent medium is important for the quality of the final product obtained and for the yield of the extraction. Preferably, the weight ratio in the method according to the present invention is of about one part of plant material to at least five parts of solvent medium.

The plant material is preferably provided as a powdered material obtained by the grinding of cereal grains, of the mesocarp or of the leaves of plants.

According to a first version, the extract from cereals according to the invention is provided in the form of an oil comprising (in percent weight):

| | |
|---|---|
| Di-O-D-galactosyl-di-O-acylglyceride | 10 to 20% |
| Triglycerides | 50 to 65% |
| Phospholipids | 10 to 20% |
| Phytosphingolipids and their glucosyle derivatives | 10 to 20% |

According to a second version, the extract from cereals according to the invention is provided in the form of a powder comprising (in percent weight):

| | |
|---|---|
| Di-O-D-galactosyl-di-O-acylglyceride | 35 to 45% |
| Phytosphingolipids | 30 to 40% |
| Glucophytosphingolipids | 10 to 20% |
| Phospholipids | 5 to 15% |

On the other hand, the plant extract according to the invention can be used for its inhibitory action against human elastase and collagenase, as a wound-healing agent, as a moisturising agent and/or as a free radical scavenger, and also as a means for enhancing the proliferation of skin fibroblasts. Furthermore, this extract can be used as a means (vector) for introducing cosmetically or pharmaceutically active agents into the intercellular space of the conjunctive tissue of the skin. Accordingly, one can use the extract, for example, for the preparation of dermatological compositions, of cosmetic compositions, of pharmaceutical compositions and/or of veterinary preparations for wound-healing and/or for treating skin problems.

Finally, the plant extract rich in Dgdg and in sphingolipids according to the invention has dietetic properties which are very interesting. The product is obtained from wheat, which, from a toxicological standpoint, is recognised as being without risk and no other solvent than ethanol is used for its extraction. Accordingly, a plant extract is obtained which makes it possible to retard skin ageing (by its moisturising action, elastase and collagenase inhibiting action) and reinforce the body defences against free radicals. The plant extract according to the invention can easily be dispersed in water or in a liquid dietetic preparation. Its addition to drinks necessitates no special method.

The present invention will be explained more in detail by means of the following examples:

EXAMPLE 1
Preparation of an Extract from Ground Wheat

Ground wheat is introduced under strong stirring into ethanol. The stirring is continued during 2 hours. The oily mixture obtained is saturated with water and it contains residual proteins. To purify the extract, one must add while stirring and before the filtration, a product for retaining the proteins and binding the water, as for example kieselguhr or celite, in a proportion ranging from 10 to 20% (weight/volume).

The mixture is then filtered with a filter having a porosity of not more than 2 μm. The filtrate rich in di-O-D-galactosyl-di-O-acylglyceride is concentrated through distillation to remove the ethanol, whereby an oil is obtained which is fluid, homogeneous and clear, dark yellow to light brown and has the overall following composition:

| | |
|---|---|
| Di-O-D-galactosyl-di-O-acylglyceride | 17% |
| Triglycerides | 55% |
| Phospholipids | 13% |
| Phytosphingolipids and glucophytosphingolipids | 15% |

This oil can be purified to extract the non-polar lipids therefrom; to this end, an emulsifier is added to the oil and the oil is heated at 70–90° C. for 30 minutes to one hour with deionised water. Thereafter, the mixture is left to stand for 24 hours. In the absence of turbulence and under the effect of gravity, the non-polar lipids which have a density lower than water form a liquid floating over a lower phase.

Freeze-drying is used for removing water from the liquid obtained. After the freeze-drying, a grinding and a micronising operation is carried out on the residue obtained, to produce an enriched powder containing from 35 to 45% of di-O-D-galactosyl-di-O-acylglyceride. This powder of exclusively vegetal origin has the following composition:

| | |
|---|---|
| Di-O-D-galactosyl-di-O-acylglyceride | 40% |
| Phytosphingolipids | 35% |
| Glucophytosphingolipids | 15% |
| Phospholipids | 10% |

Because of its highly hygroscopic properties, the powder must be placed into thick bags immediately after the manufacture, with a dehydrating agent.

The di-O-D-galactosyl-di-O-acylglyceride concentration is determined by HPLC using a column filled with silicic acid and provided with a UV detector operating at the wavelength of 214 nm. The acyl groups are derived mainly from the four following fatty acids: 18:2 (74%), 16:0 (14%), 18:1 (7%) and 18:3 (4%).

The wheat extracts containing the phytosphingolipids are essentially ceramide 3 (30 to 40%) with a small amount (2%) of associated ceramide 6 (α-OH-stearoylphytosphingosine).

A verification of the results carried out on five different preparations has shown that the variability of the concentration of the phytosphingosine was of ±12, the average percent composition thereof being:

| | |
|---|---|
| N-stearylphytosphingosine | 2.1% |
| N-oleylphytosphingosine | 7.9% |
| N-linoleylphytosphingosine | 20.4% |
| N-palmitylphytosphingosine | 4.1% |

EXAMPLE 2
Properties of the Vegetal Extracts from Wheat

A. Eye Irritation

These tests were carried out using a composition which had been freeze-dried.

The powder was solubilised at 5% in deionised water by emulsification and the liquid was introduced into the conjunctival cul-de-sac of the right eye of fully grown albino rabbits, this being carried out according to the procedure described in the OECD Directive No. 405 <<Acute eye irritation/damage>> (of the $24^{th}$ of February 1987). The results of these tests make it possible to conclude that the plant extract powder containing di-O-D-galactosyl-di-O-acylglyceride solubilised in the proportion of 5% in water is not irritating.

B. Skin Irritation

These tests were carried out with a freeze-dried composition.

The powder was solubilised at 5% in deionised water through emulsification and the liquid was applied on the back part of three fully grown albino rabbits, which back part had been shaved 24 hours before the test, this test being carried out according to the procedure described in OECD directive No. 404 <<Acute skin irritation/damage>> (of the $17^{th}$ of July 1992).

The results of these tests make it possible to conclude that the plant extract powder containing di-O-D-galactosyl-di-O-acylglyceride solubilised at 5% in water is not irritating.

These tests were confirmed by preliminary tests on humans: a 5% preparation in deionised water, solubilised by emulsification, was applied to three volunteers under an occlusive dressing during 1, 4, 8 and 24 hours and a 5% preparation in deionised water, solubilised by emulsification, was further applied to nine volunteers under an occlusive dressing during 24 hours. The evaluation of the reaction made after 24 and 48 hours showed that the product is not irritating.

C. Inhibitory Action Against Elastase

It was of interest to investigate the inhibitory action against elastase by the powder extract of the invention and to compare it with that of ceramide 3 alone. It was found that in the case of pure phytosphingolipids and of pure di-O-D-galactosyl-di-O-acylglyceride, there was practically no inhibitory activity, whereas in the case of the powder extract of the present invention, a high and direct inhibitory action against elastase is found, as well as a protective effect on the elastic tissue of the skin against degradation from the elastase of human leukocytes (EHL).

The inhibitory action of the powder extract of the invention against EHL was examined in an aqueous solution of a Tris-HCl buffer, using N-methoxysuccinyl-alanyl-alanyl-prolyl-valyl-para-nitroanilide as a synthetic substrate.

The kinetics of the reaction were determined by spectrophotometry at 405 nm, enabling the measurement of the release of para-nitroanilide, which is a coloured product. The percent inhibitory action of the preparation against the elastase was determined by comparison with a reference curve (hydrolysis of the substrate in the absence of an inhibitor).

The results indicate that 50 µg/ml (0.05 g/l) ensure a 70% reduction of the activity of the elastase. The $IC_{50}$ value (50% inhibition concentration) amounts to 30 µg/ml.

D. Inhibitory Action Against Collagenase

The extracellular matrix is comprised of a complicated network of macromolecules. The proper functioning of this conjunctive tissue is dependant on a dynamic equilibrium controlled by the three following parameters: the binding macromolecules, the proteinases degrading these binding macromolecules and specific inhibitors of these enzymes. Inflammation or ageing upset this equilibrium and causes an excessive degradation of the extracellular substances.

It was interesting to determine whether the described plant extract of the invention inhibits all the degradation processes of the macromolecules of the conjunctive tissue, and in particular if an inhibitory action against the collagenase of the conjunctive tissue acting on human fibroblasts could be demonstrated.

The test relies on the study and the quantitative determination of the activity of a specific inhibitor of the collagenase of the conjunctive tissue, namely TIMP-1 (The metalloproteinase tissue inhibitor 1) in the fibroblasts of human skin cultured in vitro. The proportion of cells exhibiting a TIMP-1 activity after the treatment is compared with that of cells exhibiting a TIMP-1 activity without a treatment (reference).

The powder extract according to the invention exerts an inhibitory action against collagenase at concentrations in excess of 10 µg/ml.

E. Enhancement of Proliferation of Skin Fibroblast

An in vitro method was applied to fibroblasts exhibiting a very high slowing-down of their proliferation. A stimulation of such aged fibroblasts to restore their proliferation is notoriously difficult. Despite of this, our studies have shown that the powder extract of the invention at the concentrations of 10 and 20 µg/ml enable a significant increase of the proliferation of skin fibroblasts. It also was found that the powdered plant extract of the invention had wound-healing properties.

F. Moisturising Effect

In the case of a pathological drying of the skin, a deficit in linoleic acid is found and this fatty acid is replaced by oleic acid.

The topical application of a cream based on the plant extract powder according to the invention (at a concentration of 0.5 to 2%) has a significant rehydrating effect on the skin.

A study carried out on seven patients shows that with a 0.5% concentration, the moisturising effect measured by means of a corneometer, achieved its maximum value after the first hour following the application, the improvement being then in excess of 50%, with a stabilisation at +30% occurring from the second hour to the eight hour. A study carried out on 20 patients with a twice daily application of a preparation containing the extract at a concentration of 2% indicates a moisturising effect substantially more important after 8 days, by comparison with patients treated with a placebo.

The topical application of the plant extract powder of the invention at a concentration of 0.5% or more improves the protection provided by the skin against moisture loss. This activity is associated with a higher linoleic acid content (in excess of 40%) and is enhanced by the effect of the phytosphingosines and of the glucosylphytosphingosines, which, as is well-known, have moisturising properties.

Actually, glucosylphytosphingosines exhibit their highest concentration in the granular layer of the epidermis (keratinocytes) where the form highly pleated multilayered structures in the Odland bodies, capable of storing high amounts of ceramides, which are necessary for the formation of conjunctive tissue between the corneous cells of the skin.

The opening of the Odland bodies by exocytosis results in the formation of the multlayered structures in the corneous layer of the skin, which is responsible for the moisture barrier properties of the skin.

The combined action of the three components, which are present in the plant extract powder of the invention, explains the exceptional activity of the plant extract for re-establishing or reinforcing the moisture-barrier properties of the skin.

G. Penetration in the Intercellular Conjunctive Tissue

The di-O-D-galactosyl-di-O-acylglyceride is a natural emulsifier which emulsifies spontaneously the plant extract powder of the invention at concentrations of 1 to 30%. Owing to this particularity, it is possible to make active the phytosphingosine naturally present in the extract, despite the fact that the solubilisation or the incorporation of a pure ceramide into a cosmetic formulation is very difficult.

The di-O-D-galactosyl-di-O-acylglyceride thus provides a penetration vector for ceramide 3 and certainly also for the entirety of the ceramide group.

One can use the above-mentioned plant extract powder as a vector for the introduction into the intercellular conjunctive tissues for the following agents: antibiotics, antimycotics, anti-herpes agents, anti-inflammatory agents, analgesics, retinoïds, ceramides, neoceramides, vitamins, flavenoïds, anthocyans, xanthins, polyphenols, vegetal extracts, polyunsaturated fatty acids, amino-acids, different polyoses, α- or β-hydroxylated acids, mineral salts, hair-removing preparations, sun-tanning preparations and sun-tanning enhancers, depigmentation preparations etc.

H. Radical Scavenging Properties

The experimental method is based on the procedure developed in 1973 by Fridovitch and McCord for SOD (J. Biol. Chem. 248, 2648).

The determination of the radical scavenging properties is based on the measurement of the inhibition or of the slowing-down of the reduction of cyto-chrome c by the product investigated, by comparison with the effect exerted by xanthin oxidase. The formation of reduced cytochrome c is monitored by spectrophotometry at 550 nm.

In these tests, a plant extract powder of the invention is used at a concentration of 1.5 mg/ml in a phosphate buffer pH 7.8 at 25° C. A slowing-down of the reduction of cytochrome c by 39.2% is thus observed.

Furthermore, an additional test was carried out with Dgdg alone, in the same conditions as above, but using the Fluka 36975 product having a purity of 95%. This test has shown that with a concentration of 0.6315 mg/ml, a slowing-down of the reduction of the cytochrome c of 36.1% is induced (the decrease obtained with the concentration of 0.6315 mg/ml corresponds to the 40% reduction obtained with 1.5 mg/ml, of the plant extract powder, if one takes into account the fact that the purity was of 95%). This indicates that the activity of the free radical scavenger of the plant extract powder, according to the invention, is associated essentially with the presence of Dgdg.

EXAMPLE 3

The cosmetic preparations according to the invention used as a vector for the plant extract can be formulated in different forms, as powders or oils, depending on the use and on the purpose: inhibition of elastase, inhibition of collagenase, wound-healing, protection against free radicals, transport, moisturising action.

| Cream No. 1 | |
|---|---|
| Glycerine | 3.00% |
| Citric acid | 0.10% |
| Tefose 2561 | 12.00% |
| Liquid PLC 2 | 4.00% |
| Solid PLC 2 | 2.00% |
| Isopropyl myristate | 1.00% |
| Tocopherol linoleate | 0.50% |
| Tylopur CB 30000 | 0.30% |
| Plant extract powder | 0.50% |
| Preservative | 1.30% |
| Perfume | 0.80 to 0.40% |
| Deionised water | to 100% |

| Cream No. 2 | |
|---|---|
| Glycerine | 3.00% |
| Citric acid | 0.20% |
| Hydrated lecithin | 0.50% |
| Solid PLC 2 | 10.00% |
| Xanthane gum | 0.30% |
| Tocopherol linoleate | 3.00% |
| Sodium carboxymethylcellulose | 1.00% |
| Hydrated coconut oil | 15.00% |
| Plant extract powder | 1.00% |
| Preservative | 1.00% |
| Perfume | 0.08 to 0.40% |
| Deionised water | to 100.00% |

| Oil-in-water emulsion | |
|---|---|
| Ester of stearic acid and of polyoxyethylene | 3.90% |
| Glycerol mono- and distearate | 0.70% |
| Cetyl alcohol | 2.45% |
| Liquid cyclic dimethylpolysiloxane | 5.00% |
| Mixture of cetylstearic alcohol and Sodium alkyle sulfate | 5.00% |
| Plant extract oil | 1 to 35% |
| Carboxyvinyl polymer | 0.20% |
| Preservative | 0.30% |
| Perfume | 0.1 to 0.4% |
| Deionised water | to 100.00% |

| Gel | |
|---|---|
| Ethanol 95% | 15.00% |
| Carboxyvinyl polymer | 30.00% |
| Plant extract powder | 0.10 to 2.00% |
| Preservative | 0.20% |
| Perfume | 0.1 to 0.4% |
| Deionised water | to 100.00% |

| Cream No. 3 | |
|---|---|
| Glycerol monostearate linked to a polyoxyethylene emulsifier | 6.00% |
| Polyoxyethylene sorbitan monostearate | 2.00% |
| Stearic acid | 2.00% |
| Cetylic acid | 1.20% |
| Liquid lanolin | 6.00% |
| Perhydrosqualene | 30.00% |
| Methylphenylpolysiloxane | 1.00% |
| Triethanolamine | 0.10% |
| Plant extract oil or | 0.50% to 5.00% |
| plant extract powder | 0.10% to 2.00% |
| Preservative | 0.30% |
| Perfume | 0.1 to 0.4% |
| Deionised water | to 100.00% |

| Shampoo No. 1 | |
|---|---|
| Lauryl-glycoside bonded to sodium lauryl-ether-sulfate | 11.00% |
| Cocoamidopropyl-betaine | 3.00% |
| Cellulose acetate | 1.00% |
| Laurylpyrrolidone | 1.50% |
| Propylene glycol | 2.00% |
| Emulsion of a 10% plant extract powder | 2.00 to 5.00% |
| Deionised water | to 100.00% |

| Shampoo No. 2 (for frequent use) | |
|---|---|
| Sodium lauryl-ether-sulfate | 44.00% |
| Isopropyle myristate | 1.80% |
| Oleic alcohol | 0.60% |
| PEG 15 - cocopolyamine | 5.00% |
| Sodium chloride | 0.28% |
| Emulsion of 10% plant extract powder | 2.00 to 5.00% |
| Preservative | 0.25% |
| Deionised water | to 100.00% |

| Shampoo No. 3 (for babies) | |
|---|---|
| Texapon ASV | 4.00% |
| Preservative | 0.60% |
| Orange-flower water | 10.00% |
| Emulsion of 10% plant extract powder | 2.00 to 5.00% |
| Deionised water | to 100.00% |

EXAMPLE 4

One can prepare a dietetic drink with a wheat extract by simple mixing, to obtain, for example, the following formulation:

| | |
|---|---|
| Fructose | 5.0 g |
| Wheat extract oil | 0.1 g |
| Vitamin E linoleate | |
| β-carotene | 1.5 g |
| Flavouring agent | 1 to 5 g |
| Preservative | as needed |
| Water | to 100 g |

The increase in the radical scavenging activity of a drink with a very low activity achieved through the addition of a wheat extract (oil) is substantial and is due in particular to Dgdg, as can be seen from the following table.

| Drink | Radical scavenging activity, in vitro |
|---|---|
| Reference (T) | 4% |
| T + wheat extract (0.005% of Dgdg) | 9% |
| T + wheat extract (0.020% of Dgdg) | 17% |
| T + wheat extract (0.040% of Dgdg) | 26% |

What is claimed is:

1. A plant extract comprising di-O-D-galactosyl-di-O-acyl-glyceride; phytosphingolipids and phospholipids obtained by a process comprising the steps of:
   (a) treating about one part of a plant with at least five parts of cold ethanol to obtain a mixture containing oil, water and proteins,
   (b) adding to said mixture a product for retaining the proteins and binding the water, and
   (c) filtering said mixture with a filter having a porosity of not more than 2 μm.

2. The plant extract according to claim 1 which is dried and in powder form and comprises:
   di-O-D-galactosyl-di-O-acylglyceride between 35 to 40 wt %,
   phytosphingolipids between 30 to 40 wt %,
   glycosylphytosphingolipids between 10 to 20 wt %, and
   phospholipids between 5 to 15 wt %.

3. The plant extract according to claim 1 which is dried and in an oily form and comprises:
   di-O-D-galactosyl-di-O-acylglyceride between 10 to 20 wt %, triglycerides between 50 to 65 wt %, phytosphingolipids, and glycosylphytosphingolipids between 10 to 20 wt %.

4. A plant extract comprising as essential constituents di-O-D-galactosyl-di-O-acyl-glyceride, phytosphingolipids and phospholipids obtained by a process comprising the steps of
  (a) treating about one part of a plant with at least five parts of cold ethanol to obtain a mixture containing oil, water and proteins,
  (b) adding to said mixture a product for retaining the proteins and binding the water,
  (c) filtering said mixture with a filter having a porosity of not more than 2 μm,
  (d) extracting non-polar lipids from the filtrate obtained in step (c), and
  (e) removing water from the filtrate obtained in step (d).

5. The plant extract according to claim 4 comprising as essential constituents di-O-D-galactosyl-di-O-acyl-glyceride, phytosphingolipids and phospholipids, in the following proportions:

di-O-D-galactosyl-di-O-acylglyceride between 35 to 40 wt %, phytosphingolipids between 30 to 40 wt %, glycosylphytosphingolipids between 10 to 20 wt %, and phospholipids between 5 to 15 wt %.

6. An emulsion for a cosmetic or a pharmaceutical comprising the plant extract according to claim 2 in a weight proportion ranging from 1 to 35%.

7. The emulsion according to claim 6 wherein said plant extract is an extract of wheat grain.

8. The emulsion for a cosmetic or a pharmaceutical composition comprising the plant extract according to claim 5, in a weight proportion ranging from 1 to 35%.

9. The emulsion according to claim 8, wherein said plant extract is an extract of wheat grain.

10. A plant extract according to claim 4 which is an extract of wheat grain.

* * * * *